United States Patent
Wilson et al.

(10) Patent No.: US 9,126,139 B2
(45) Date of Patent: Sep. 8, 2015

(54) CARBON ADSORBENT FOR HYDROGEN SULFIDE REMOVAL FROM GASES CONTAINING SAME, AND REGENERATION OF ADSORBENT

(71) Applicant: Entegris, Inc., Billerica, MA (US)

(72) Inventors: Shaun M. Wilson, Trumbull, CT (US); Edward A. Sturm, New Milford, CT (US); Michael J. Wodjenski, New Milford, CT (US); J. Donald Carruthers, Fairfield, CT (US); Joshua B. Sweeney, Katonah, NY (US)

(73) Assignee: ENTEGRIS, INC., Billerica, MA (US)

( * ) Notice: Subject to any disclaimer, the term of this patent is extended or adjusted under 35 U.S.C. 154(b) by 0 days.

(21) Appl. No.: 13/904,988

(22) Filed: May 29, 2013

(65) Prior Publication Data

US 2013/0324397 A1 Dec. 5, 2013

Related U.S. Application Data

(60) Provisional application No. 61/652,348, filed on May 29, 2012.

(51) Int. Cl.
*B01D 53/04* (2006.01)
*B01J 20/20* (2006.01)
(Continued)

(52) U.S. Cl.
CPC .......... *B01D 53/04* (2013.01); *B01D 53/02* (2013.01); *B01J 20/20* (2013.01);
(Continued)

(58) Field of Classification Search
CPC ...... B01D 53/04; B01J 20/20; B01J 20/3078; Y02C 20/20
USPC ............. 502/416; 423/445 R; 95/95, 96, 136; 96/108, 115, 125, 136, 143; 526/823
See application file for complete search history.

(56) References Cited

U.S. PATENT DOCUMENTS

| 240,423 A | 4/1881 | James |
|---|---|---|
| 1,608,155 A | 11/1926 | Barnebey |

(Continued)

FOREIGN PATENT DOCUMENTS

| CN | 101362595 A | 2/2009 |
|---|---|---|
| CN | 101903081 A | 12/2010 |

(Continued)

OTHER PUBLICATIONS

Xu, Bin, et al. "An activation-free method for preparing microporous carbon by the pyrolysis of poly (vinylidene fluoride)." Carbon 48.10 (2010): 2812-2814.*

(Continued)

*Primary Examiner* — Richard M Rump (74) *Attorney, Agent, or Firm* — Hultquist, PLLC; Steven J. Hultquist; John Pillion (57) ABSTRACT

A durable carbon pyrolyzate adsorbent having reversible sorptive affinity for hydrogen sulfide, and including the following characteristics: (a) a bulk density as measured by ASTM D2854 in a range of from 0.55 g/cc adsorbent to 1.25 g/cc adsorbent; (b) an $H_2S$ capacity in a range of from 140 cc $H_2S$/g adsorbent to 250 cc $H_2S$/g adsorbent, at normal conditions (1 atm, 293.15° K); (c) an $H_2S$ capacity in a range of from 1.0 cc $H_2S$/g adsorbent to 15.0 cc $H_2S$/g adsorbent, at partial pressure of 0.76 torr (101.3 Pa) (1000 ppm) of $H_2S$ at 293.15° K; and (d) a single pellet radial crush strength in a range of from 7 kilopond (kP) to 40 kilopond (kP) as measured by ASTM D4179. Such adsorbent is usefully employed for capture of hydrogen sulfide from gases containing same, such as $H_2S$-containing gas associated with flowable hydrocarbonaceous material in refining operations, biogas produced by biomass digesters, gas mixtures produced by fluid catalytic cracking (FCC) units, and effluents from power plants gasifying sulfur-containing coal in an integrated gasification combined cycle (IGCC) process.

20 Claims, 3 Drawing Sheets

(51) Int. Cl.
*B01J 20/30* (2006.01)
*B01J 20/34* (2006.01)
*B01J 20/28* (2006.01)
*B01D 53/02* (2006.01)
*C12M 1/00* (2006.01)

(52) U.S. Cl.
CPC ....... *B01J 20/28011* (2013.01); *B01J 20/3078* (2013.01); *B01J 20/3416* (2013.01); *C12M 47/18* (2013.01); *B01D 2253/102* (2013.01); *B01D 2257/304* (2013.01); *B01D 2258/05* (2013.01); *Y02C 20/20* (2013.01)

(56) References Cited

U.S. PATENT DOCUMENTS

| | | |
|---|---|---|
| 1,714,245 A | 5/1929 | Schaefer |
| 2,356,334 A | 8/1944 | Maude et al. |
| 2,423,702 A | 7/1947 | Hart |
| 2,450,289 A | 9/1948 | Marek |
| 2,663,626 A | 12/1953 | Spangler |
| 2,971,607 A | 2/1961 | Caswell |
| 2,987,139 A | 6/1961 | Bush |
| 2,997,371 A | 8/1961 | Wadsworth et al. |
| 3,006,153 A | 10/1961 | Cook |
| 3,080,307 A | 3/1963 | Rinald |
| 3,093,564 A | 6/1963 | Weisman et al. |
| 3,116,132 A | 12/1963 | Haller et al. |
| 3,144,200 A | 8/1964 | Taylor et al. |
| 3,264,803 A | 8/1966 | Read |
| 3,287,432 A | 11/1966 | Sensel |
| 3,415,069 A | 12/1968 | Hauser |
| 3,469,375 A | 9/1969 | Barrington et al. |
| 3,539,467 A | 11/1970 | Bozarth et al. |
| 3,675,392 A | 7/1972 | Reighter |
| 3,713,273 A | 1/1973 | Coffee |
| 3,719,026 A | 3/1973 | Sand |
| 3,788,036 A | 1/1974 | Lee et al. |
| 3,884,830 A | 5/1975 | Grant |
| 3,912,472 A | 10/1975 | Marble |
| 4,000,236 A | 12/1976 | Redfarn et al. |
| 4,023,701 A | 5/1977 | Dockery |
| 4,046,709 A | 9/1977 | Yuki |
| 4,063,912 A | 12/1977 | Neely et al. |
| 4,082,694 A | 4/1978 | Wennerberg et al. |
| 4,139,416 A | 2/1979 | Palumbo et al. |
| 4,263,018 A | 4/1981 | McCombs et al. |
| 4,302,224 A | 11/1981 | McCombs et al. |
| 4,343,770 A | 8/1982 | Simons |
| 4,373,938 A | 2/1983 | McCombs |
| 4,378,982 A | 4/1983 | McCombs |
| 4,386,947 A | 6/1983 | Mizuno et al. |
| 4,414,005 A | 11/1983 | De Bievre et al. |
| 4,526,887 A | 7/1985 | Sutt, Jr. |
| 4,528,281 A | 7/1985 | Sutt, Jr. |
| 4,540,678 A | 9/1985 | Sutt, Jr. |
| 4,578,256 A | 3/1986 | Nishino et al. |
| 4,723,967 A | 2/1988 | Tom |
| 4,738,693 A | 4/1988 | Tom |
| 4,738,694 A | 4/1988 | Godino et al. |
| 4,738,753 A | 4/1988 | Corato et al. |
| 4,744,221 A | 5/1988 | Knollmueller |
| 4,749,384 A | 6/1988 | Nowobilski et al. |
| 4,788,973 A | 12/1988 | Kirchgeorg et al. |
| 4,830,643 A | 5/1989 | Sassa et al. |
| 4,847,494 A | 7/1989 | Alvarez |
| 4,880,765 A | 11/1989 | Knoblauch et al. |
| 4,881,958 A | 11/1989 | Eckardt et al. |
| 4,920,270 A | 4/1990 | Grodzins |
| 4,957,897 A | 9/1990 | Maroldo et al. |
| 4,964,524 A | 10/1990 | Halene |
| 4,967,934 A | 11/1990 | Andonian |
| 4,989,160 A | 1/1991 | Garrett et al. |
| 5,051,117 A | 9/1991 | Prigge et al. |
| 5,071,820 A | 12/1991 | Quinn et al. |
| 5,089,244 A | 2/1992 | Parent et al. |
| 5,104,530 A | 4/1992 | Maroldo et al. |
| 5,110,328 A | 5/1992 | Yokota et al. |
| 5,112,367 A | 5/1992 | Hill |
| 5,133,787 A | 7/1992 | Diot et al. |
| 5,151,395 A | 9/1992 | Tom |
| 5,202,096 A | 4/1993 | Jain |
| 5,213,769 A | 5/1993 | Whitlock |
| 5,238,469 A | 8/1993 | Briesacher et al. |
| 5,356,852 A | 10/1994 | DeLiso et al. |
| 5,372,619 A | 12/1994 | Greinke et al. |
| 5,376,609 A | 12/1994 | Guile |
| 5,409,526 A | 4/1995 | Zheng et al. |
| 5,416,056 A | 5/1995 | Baker |
| 5,417,742 A | 5/1995 | Tamhankar et al. |
| 5,429,662 A | 7/1995 | Fillet |
| 5,512,087 A | 4/1996 | Varner et al. |
| 5,518,528 A | 5/1996 | Tom et al. |
| 5,549,736 A | 8/1996 | Coffield et al. |
| 5,614,459 A | 3/1997 | Mondragon et al. |
| 5,658,372 A | 8/1997 | Gadkaree |
| 5,674,462 A | 10/1997 | Hayden et al. |
| 5,676,735 A | 10/1997 | McManus |
| 5,704,965 A | 1/1998 | Tom et al. |
| 5,704,967 A | 1/1998 | Tom et al. |
| 5,707,424 A | 1/1998 | Tom et al. |
| 5,710,092 A | 1/1998 | Baker |
| 5,744,421 A | 4/1998 | Robinson et al. |
| 5,800,596 A | 9/1998 | Collin et al. |
| 5,833,936 A | 11/1998 | Euzen et al. |
| 5,837,741 A | 11/1998 | Schwarz et al. |
| 5,846,639 A | 12/1998 | Robinson et al. |
| 5,851,270 A | 12/1998 | Olander |
| 5,851,403 A | 12/1998 | Petrisko et al. |
| 5,876,487 A | 3/1999 | Dahlgren et al. |
| 5,902,562 A | 5/1999 | Lagasse et al. |
| 5,912,424 A | 6/1999 | Judkins et al. |
| 5,914,294 A | 6/1999 | Park et al. |
| 5,917,140 A | 6/1999 | Tom |
| 5,935,305 A | 8/1999 | Tom et al. |
| 5,961,697 A | 10/1999 | McManus et al. |
| 5,965,483 A | 10/1999 | Baker et al. |
| 5,972,253 A | 10/1999 | Kimber |
| 5,993,766 A | 11/1999 | Tom et al. |
| 6,006,797 A | 12/1999 | Buelow et al. |
| 6,019,823 A | 2/2000 | Tischler et al. |
| 6,030,698 A | 2/2000 | Burchell et al. |
| 6,089,027 A | 7/2000 | Wang et al. |
| 6,101,816 A | 8/2000 | Wang et al. |
| 6,132,492 A | 10/2000 | Hultquist et al. |
| 6,155,289 A | 12/2000 | Carlsen et al. |
| 6,156,697 A | 12/2000 | Gadkaree |
| 6,171,373 B1 | 1/2001 | Park et al. |
| 6,187,713 B1 | 2/2001 | Gadkaree |
| 6,207,264 B1 | 3/2001 | Robinson et al. |
| 6,225,257 B1 | 5/2001 | Putyera et al. |
| 6,258,300 B1 | 7/2001 | Burchell et al. |
| 6,284,705 B1 | 9/2001 | Park et al. |
| 6,298,515 B1 | 10/2001 | Robinson |
| 6,309,446 B1 | 10/2001 | Nakanoya et al. |
| 6,309,449 B1 | 10/2001 | Klos et al. |
| 6,406,519 B1 | 6/2002 | Tom et al. |
| 6,436,175 B1 | 8/2002 | Coates et al. |
| 6,453,924 B1 | 9/2002 | Wang et al. |
| 6,475,411 B1 | 11/2002 | Burchell et al. |
| 6,475,461 B1 | 11/2002 | Ohsaki et al. |
| 6,500,238 B1 | 12/2002 | Brandes et al. |
| 6,521,019 B2 | 2/2003 | Jain et al. |
| 6,561,213 B2 | 5/2003 | Wang et al. |
| 6,592,653 B2 | 7/2003 | Wang et al. |
| 6,626,981 B2 | 9/2003 | Wojtowicz et al. |
| 6,670,304 B2 | 12/2003 | Chang |
| 6,699,561 B2 | 3/2004 | Wolff |
| 6,743,278 B1 | 6/2004 | Carruthers |
| 6,764,755 B2 | 7/2004 | Tom et al. |
| 6,793,718 B2 | 9/2004 | Mochizuki et al. |
| 6,939,394 B2 | 9/2005 | Carruthers |
| 6,991,671 B2 | 1/2006 | Brestovansky et al. |
| D545,393 S | 6/2007 | Brestovansky et al. |

(56) References Cited

U.S. PATENT DOCUMENTS

| | | | |
|---|---|---|---|
| 7,285,154 B2 | 10/2007 | Karwacki, Jr. et al. | |
| 7,455,719 B2* | 11/2008 | Carruthers | 95/90 |
| 7,494,530 B2 | 2/2009 | Carruthers | |
| 7,501,010 B2 | 3/2009 | Brestovansky et al. | |
| 7,972,421 B2 | 7/2011 | Brestovansky et al. | |
| 8,002,880 B2 | 8/2011 | Carruthers | |
| 8,282,714 B2 | 10/2012 | Carruthers | |
| 2002/0020292 A1 | 2/2002 | Wojtowicz et al. | |
| 2002/0073847 A1 | 6/2002 | Sheline et al. | |
| 2002/0194989 A1 | 12/2002 | Tuma et al. | |
| 2003/0000385 A1 | 1/2003 | Kawai et al. | |
| 2003/0145731 A1 | 8/2003 | Biasio | |
| 2003/0157014 A1 | 8/2003 | Wang et al. | |
| 2003/0196553 A1 | 10/2003 | Mochizuki et al. | |
| 2003/0205581 A1 | 11/2003 | Wertenberger | |
| 2004/0107838 A1 | 6/2004 | Carruthers | |
| 2005/0014643 A1 | 1/2005 | Lini et al. | |
| 2009/0038477 A1 | 2/2009 | Abe et al. | |
| 2009/0107331 A1 | 4/2009 | Urakami | |
| 2009/0173225 A1 | 7/2009 | Brestovansky et al. | |
| 2009/0258782 A1 | 10/2009 | Gogotsi et al. | |
| 2009/0304570 A1 | 12/2009 | Kim et al. | |
| 2010/0142122 A1 | 6/2010 | Tanaka | |
| 2011/0094159 A1 | 4/2011 | Moeller | |
| 2012/0024157 A1* | 2/2012 | Maheshwary et al. | 96/133 |
| 2012/0180660 A1 | 7/2012 | Wilson et al. | |
| 2012/0325850 A1 | 12/2012 | Carruthers | |
| 2013/0112076 A1 | 5/2013 | Baum et al. | |
| 2013/0298769 A1* | 11/2013 | Petruska et al. | 95/139 |

FOREIGN PATENT DOCUMENTS

| | | |
|---|---|---|
| DE | 1095796 A | 12/1960 |
| DE | 2264512 A | 1/1974 |
| DE | 3139781 A1 | 4/1983 |
| EP | 0344917 A1 | 12/1989 |
| EP | 0860640 A1 | 8/1998 |
| EP | 0891943 A1 | 1/1999 |
| EP | 1064996 A1 | 1/2001 |
| EP | 1072839 A2 | 1/2001 |
| FR | 2550466 A1 | 2/1985 |
| GB | 1385922 A | 3/1975 |
| GB | 2232364 A | 12/1990 |
| JP | 52-72373 A | 6/1977 |
| JP | 55-73315 A | 6/1980 |
| JP | 56-158087 A | 12/1981 |
| JP | 56-158126 A | 12/1981 |
| JP | 60-150831 A | 8/1985 |
| JP | 61-133116 A | 6/1986 |
| JP | 61-144495 A | 7/1986 |
| JP | 63-88017 A | 4/1988 |
| JP | 1-131015 A | 5/1989 |
| JP | 2-66399 A | 3/1990 |
| JP | 4-224102 A | 8/1992 |
| JP | 7-124468 A | 5/1995 |
| JP | 08-504394 A | 5/1996 |
| JP | 9-242995 A | 9/1997 |
| JP | 11-82891 A | 3/1999 |
| JP | 11-511233 A | 9/1999 |
| JP | 2000-28098 A | 1/2000 |
| JP | 2000-500842 A | 1/2000 |
| JP | 2000-205496 A | 7/2000 |
| JP | 2001-287905 A | 10/2001 |
| JP | 2002-102689 A | 4/2002 |
| JP | 2002-156097 A | 5/2002 |
| JP | 2002-158021 A | 5/2002 |
| JP | 2003-535803 A | 12/2003 |
| JP | 2006-7127 A | 1/2006 |
| TW | 386890 B | 4/2000 |
| WO | 9407794 A1 | 4/1994 |
| WO | 9500234 A1 | 1/1995 |
| WO | 9611739 A1 | 4/1996 |
| WO | 9716509 A1 | 5/1997 |
| WO | 9744118 A1 | 11/1997 |
| WO | 9747382 A1 | 12/1997 |
| WO | 9830496 A1 | 7/1998 |
| WO | 9941010 A1 | 8/1999 |
| WO | 9959700 A1 | 11/1999 |
| WO | 0015330 A1 | 3/2000 |
| WO | 0193985 A1 | 12/2001 |
| WO | 0224310 A1 | 3/2002 |
| WO | 02051525 A1 | 7/2002 |
| WO | 02068324 A1 | 9/2002 |
| WO | 03092778 A1 | 11/2003 |
| WO | 2009011750 A2 | 1/2009 |
| WO | 2012106218 A2 | 8/2012 |
| WO | 2012145337 A1 | 10/2012 |

OTHER PUBLICATIONS

Sing, K., et al., "Reporting Physisorption Data for Gas/Solid Systems with Special Reference to the Determination of Surface Area and Porosity", "Pure Appl. Chem.", 1985, pp. 603-619, vol. 57, No. 4.

Unpublished U.S. Appl. No. 13/857,385, filed Apr. 5, 2013.

Unpublished U.S. Appl. No. 13/981,376, filed Jul. 24, 2013.

Unpublished U.S. Appl. No. 14/111,547, filed Oct. 12, 2013.

Wojtowicz, M., et al., "Macroporous Carbon Adsorbents for Hydrogen Storage", "Int. J. Soc. of Mater. Eng. Resour.", 1999, pp. 253-266, vol. 7, No. 2.

Air Products and Chemicals, Inc., "XeCovery: A New Onsite Xenon Recovery Service by Air Products", "www.airproducts.com/electronics/technologies/xecovery.htm (Accessed on Jun. 4, 2010)", pp. 12.

Carrott, P., et al., "A New Method for the Determination of Micropore Size Distributions", "Studies in Surface Science and Catalysis: Characterization of Porous Solids", 1988, pp. 89-100, vol. 39.

Dacey, J., et al., "Adsorption on Saran Charcoal: A New Type of Molecular Sieve", "Trans. Faraday Soc.", Mar. 6, 1954, pp. 740-748, vol. 50.

Dacey, J., et al., "The formation of carbon from polyvinylidene chloride", "Proceedings of the Fourth Conference on Carbon", 1960, pp. 315-319.

Macdonald, J., et al., "Carbon Adsorbents for Natural Gas Storage", "Fuel", Jan. 1998, pp. 61-64, vol. 77, No. 1/2.

Parkyns, N., et al., "Chapter 11: Natural Gas Adsorbed on Carbon", "Porosity in Carbons: Characterization and Applications", 1995, pp. 291-325.

Polarz, S., et al., "Nanoporous Materials", "Journal of Nanoscience and Nanotechnology", Dec. 2002, pp. 581-612, vol. 2, No. 6.

Quinn, D., et al., "Natural Gas Storage", "Carbon", Feb. 1992, pp. 1097-1103, vol. 30, No. 7.

Rouquerol, F., et al., "Chapter 9.5.4: Adsorption of water vapour", "Adsorption by Powders and Porous Solids: Principles, Methodology, and Applications", Oct. 1998, pp. 276-277.

Bagreev, A., et al, "Desulfurization of digester gas: prediction of activated carbon bed performance at low concentrations of hydrogen sulfide", "Catalysis Today", Dec. 15, 2004, pp. 329-337, vol. 99.

Jimenez-Cruz, F., et al, "Adsorption of n-Heptane and 2-Methylheptane in the Gas Phase on Polyvinylidene Chloride-Based Microporous Activated Carbon", "Energy and Fuels", Aug. 17, 2007, pp. 2929-2934, vol. 21.

Jung, H., et al, "Pore Structure Characterization of Poly(vinylidene chloride)-Derived Nanoporous Carbons", "Carbon Letters", Oct. 31, 2012, pp. 236-242, vol. 13, No. 4.

\* cited by examiner

CARBON ADSORBENT FOR HYDROGEN SULFIDE REMOVAL FROM GASES CONTAINING SAME, AND REGENERATION OF ADSORBENT

CROSS-REFERENCE TO RELATED APPLICATION

The benefit of priority under 35 USC 119(e) of U.S. Provisional Patent Application No. 61/652,348 filed May 29, 2012 in the names of Shaun M. Wilson, et al. for "CARBON ADSORBENT FOR HYDROGEN SULFIDE REMOVAL FROM GASES CONTAINING SAME, AND REGENERATION OF ADSORBENT" is hereby claimed. The disclosure of U.S. Provisional Patent Application No. 61/652,348 is hereby incorporated herein by reference, in its entirety, for all purposes

FIELD

The present disclosure relates to adsorptive removal of hydrogen sulfide from gas mixtures including same, e.g., natural gas, biogas from a digester, or syngas from a coal gasification process containing hydrogen sulfide as an undesired contaminant thereof.

DESCRIPTION OF THE RELATED ART

Hydrogen sulfide ($H_2S$) is a toxic and flammable gas that is present in varying concentrations in both crude oil and natural gas.

While the odor threshold for $H_2S$ is quite low (500 ppt), the human olfactory system actually loses sensitivity to it with extended exposure above approximately 100 ppm, and $H_2S$ can be lethal at concentrations above 500 ppm. In addition to the environmental, health and safety issues associated with $H_2S$, its presence can poison certain reactions and processes, and its release can also cause plant shut-downs based on levels detected by personnel monitoring devices.

As such, petroleum refineries must take precautions to protect both personnel and the environment from the potentially harmful effects of hydrogen sulfide.

One operation in a refinery that is prone to cause releases of $H_2S$ is the cleaning or vacuuming of "slop oil" storage tanks, which contain a myriad of different hydrocarbons, water, and $H_2S$. During this cleaning operation, the exhaust from vacuum pumper trucks is typically released to the atmosphere.

In natural gas, the presence of hydrogen sulfide is detrimental from a number of perspectives. In addition to its toxicity, hydrogen sulfide is corrosive in natural gas pipelines. It typically is desirable to reduce concentrations of hydrogen sulfide in natural gas to below 25 ppm before the gas is introduced to pipelines. Since hydrogen sulfide occurs naturally in most gas reservoirs, this presents a significant challenge.

In addition to the foregoing applications in which hydrogen sulfide is desirably removed from gas mixtures containing same, hydrogen sulfide may be a significant component of synthetic gases generated in the gasification of coals in IGCC plants. In such power generation operations, hydrogen sulfide and other acid gases are desirably captured and removed prior to the gas turbines, to protect the turbines and to meet regulatory constraints and practical considerations of sulfur recovery.

SUMMARY

The present disclosure relates to adsorbent materials and adsorption processes, including, without limitation, adsorptive removal of hydrogen sulfide from gas mixtures containing same, e.g., natural gas, biogas from a digester, or syngas from a coal gasification process containing hydrogen sulfide as an undesired contaminant thereof.

The disclosure relates in one aspect to a durable and robust carbon adsorbent having reversible sorptive affinity for hydrogen sulfide, and comprising the following characteristics:

(a) a bulk density, as measured by ASTM D2854, in a range of from 0.55 g/cc adsorbent to 1.25 g/cc adsorbent, preferably in a range of from 0.60 g/cc to 1.15 g/cc, and most preferably in a range of from 0.65 g/cc to 1.00 g/cc;

(b) an $H_2S$ capacity in a range of from 140 cc $H_2S$/g adsorbent to 250 cc $H_2S$/g adsorbent, at normal conditions (1 atm, 293.15° K);

(c) an $H_2S$ capacity in a range of from 1.0 cc $H_2S$/g to 15 cc $H_2S$/g adsorbent, preferably in a range of from 1.0 cc $H_2S$/g to 10 cc $H_2S$/g adsorbent, and most preferably in a range of from 1.0 cc $H_2S$/g to 5 cc $H_2S$/g adsorbent, at partial pressure of 0.76 torr (101.3 Pa) (1000 ppm) of $H_2S$ at 293.15° K; and (d) a single pellet radial crush strength, as measured by ASTM D4179, for a nominal 3 mm pellet, in a range of from 7 kilopond (kP) to 40 kilopond (kP), preferably in a range of from 9 kP to 35 kP, and most preferably in a range of from 11 kP to 30 kP.

In another aspect, the disclosure relates to an apparatus for removing hydrogen sulfide from a hydrogen sulfide-containing gas, such apparatus comprising a vessel containing a carbon adsorbent of the present disclosure, wherein the vessel is adapted for contacting of the gas with the carbon adsorbent to effect adsorption of hydrogen sulfide by the adsorbent, to yield a hydrogen sulfide-reduced gas.

The disclosure relates in another aspect to a method of making a carbon adsorbent of the present disclosure, such method comprising pyrolyzing a pyrolyzable starting material for sufficient time under sufficient pyrolysis conditions to yield said carbon adsorbent, wherein the pyrolyzable starting material comprises a resin selected from the group consisting of polyethylene, polyolefins, phenolic resins, acrylic resins, polyurethane resins, fluoropolymer resins, polyvinyl chloride, polyvinylidene chloride, polyvinylidene fluoride, polytetrafluoroethylene, and copolymers of monomers of the foregoing resins.

A still further aspect the disclosure relates to a method of removing hydrogen sulfide from a gas mixture including same, such method comprising contacting said gas mixture with a carbon adsorbent of the present disclosure, to adsorb hydrogen sulfide from the gas mixture on the adsorbent and yield a hydrogen sulfide-reduced gas.

In another aspect, the disclosure relates to a process for capture of hydrogen sulfide present in a gas associated with a flowable hydrocarbonaceous material, such process comprising: separating the hydrogen sulfide-containing gas from the hydrocarbonaceous material; and contacting the hydrogen sulfide-containing gas with a carbon adsorbent of the present disclosure so that the carbon adsorbent adsorbs the hydrogen sulfide from the hydrogen sulfide-containing gas to yield a hydrogen sulfide-reduced gas.

Other aspects, features and embodiments of the disclosure will be more fully apparent from the ensuing description and appended claims.

DETAILED DESCRIPTION

The present invention relates to adsorbents and adsorption apparatus and processes for sorptively removing hydrogen sulfide from gas mixtures containing same.

The present disclosure reflects the discovery of adsorbents that are usefully employed to separate hydrogen sulfide from gas mixtures containing hydrogen sulfide, e.g., hydrogen sulfide/methane gas mixtures, hydrogen sulfide-containing effluent gases from IGCC power plants producing syngas via gasification of sulfur-containing coal, etc.

The present disclosure in one aspect relates to a carbon adsorbent having sorptive affinity for hydrogen sulfide, and comprising the following characteristics:

(a) a bulk density, as measured by ASTM D2854, in a range of from 0.55 g/cc adsorbent to 1.25 g/cc adsorbent, preferably in a range of from 0.60 g/cc to 1.15 g/cc, and most preferably in a range of from 0.65 g/cc to 1.00 g/cc;

(b) an $H_2S$ capacity in a range of from 140 cc $H_2S$/g adsorbent to 250 cc $H_2S$/g adsorbent, at normal conditions (1 atm, 293.15° K);

(c) an $H_2S$ capacity in a range of from 1.0 cc $H_2S$/g to 15 cc $H_2S$/g adsorbent, preferably in a range of from 1.0 cc $H_2S$/g to 10 cc $H_2S$/g adsorbent, and most preferably in a range of from 1.0 cc $H_2S$/g to 5 cc $H_2S$/g adsorbent, at partial pressure of 0.76 torr (101.3 Pa) (1000 ppm) of $H_2S$ at 293.15° K; and (d) a single pellet radial crush strength, as measured by ASTM D4179, for a nominal 3 mm pellet, in a range of from 7 kilopond (kP) to 40 kilopond (kP), preferably in a range of from 9 kP to 35 kP, and most preferably in a range of from 11 kP to 30 kP.

In some embodiments, the carbon adsorbent is additionally characterized by (e) total ash content, as measured by ASTM D2866, of less than 1%, preferably ≤0.7%, and most preferably ≤0.5%.

In various embodiments, the carbon adsorbent of the disclosure includes adsorbents that have sorptive affinity for hydrogen sulfide and exhibit the characterizable qualities, parameters and criteria variously disclosed herein. It will be appreciated that the adsorbents of the present disclosure include adsorbents having various combinations of such qualities, parameters and criteria, and that any of such individual characteristics, or specific one(s) thereof, may be aggregated in any suitable manner to particularize carbon pyrolyzate adsorbents useful for adsorption of hydrogen sulfide thereon. The carbon adsorbent of the present disclosure may suitably comprise a carbon pyrolyzate material, as a carbon pyrolyzate adsorbent.

The durable carbon adsorbent of the present disclosure, having reversible sorptive affinity for hydrogen sulfide, may in specific embodiments have a bulk density in a range of from 0.55 to 1.25 g/cc adsorbent. The bulk density of the adsorbent in various other embodiments can be in a range of: from 0.6 to 1.15 g/cc adsorbent; from 0.65 to 1.0 g/cc adsorbent; from 0.6 to 0.9 g/cc adsorbent; from 0.6 to 0.75 g/cc adsorbent; from 0.65 to 0.73 g/cc adsorbent; from 0.6 to 1.3 g/cc of adsorbent; from 0.65 to 1.25 g/cc of adsorbent; or from 0.7 to 1.15 g/cc of adsorbent. It will be recognized that the bulk density of suitable materials of the disclosure can be widely varied in practice, to provide carbon adsorbents of suitable character for hydrogen sulfide adsorption applications.

The carbon adsorbent of the present disclosure is robust and durable in character, meaning that it is capable of undergoing repeated reversible sorption (adsorption/desorption) cycles over long periods of time, without loss of sorptive capacity, or deterioration of performance.

Preferred adsorbents of the present disclosure have an $H_2S$ capacity that is in a range of from 150 cc/g adsorbent to 250 cc/g adsorbent at normal conditions (1 atm, 293.15° K), and it a range of from 1.4 cc/g adsorbent to 15 cc/g adsorbent, at a partial pressure of 0.76 torr (101.3 Pa) (1000 ppm) of $H_2S$ at 293.15° K.

Adsorbents of the present disclosure in various embodiments have a single pellet radial crush strength that is in a range of from 7 kilopond (kP) to 40 kilopond (kP) as measured by the procedure of American Society of Testing Materials (ASTM) method D4179. In other embodiments, the adsorbent may have a single pellet radial crush strength in a range of from 9 kilopond (kP) to 35 kilopond (kP) as measured by the procedure of American Society of Testing Materials (ASTM) method D4179. In still other embodiments, the adsorbent may have a single pellet radial crush strength in a range of from 11 kilopond (kP) to 30 kilopond (kP) as measured by the procedure of American Society of Testing Materials (ASTM) method D4179.

In and illustrative specific embodiment, the carbon adsorbent of the disclosure is of tablet form wherein individual tablet articles have a diameter of 3.20 mm and a thickness of 2.18 mm, with a bulk density of from 0.65 to 0.73 g/cc adsorbent. Such adsorbent has an $H_2S$ capacity that is greater than 150 cc/g adsorbent at normal conditions (1 atm, 293.15° K) and greater than 1.4 cc/g adsorbent at a partial pressure of 0.76 torr (101.3 Pa) (1000 ppm) of $H_2S$ at 293.15° K. This carbon pyrolyzate adsorbent is stable at temperature up to 180° C. and has a single pellet radial crush strength of greater than 11 kilopond (kP) as measured by the procedure of American Society of Testing Materials (ASTM) method D4179.

The carbon adsorbent of the disclosure in various embodiments can be of any suitable form, e.g., a monolith, tablet, pellet, extrudate, or powder form. The adsorbent is usefully employed in various embodiments in particulate form. In one embodiment, the adsorbent is in a tablet form, e.g., with an average piece diameter (major length dimension) that is in a range of from 1.0 to 5 mm. In another embodiment, the carbon adsorbent is in a particulate form comprising particles of particle size in a range of from 0.8 to 3.0 mm. In other embodiments, the carbon adsorbent can be in a monolithic form, such as of brick, block, bar, disc, columnar, or other conformation appropriate to the end use of the adsorbent.

The carbon adsorbent in various embodiments advantageously comprises fines at concentration of less than 1% by weight, based on weight of the adsorbent.

Carbon pyrolyzate adsorbents of the disclosure in various embodiments are regenerable using vacuum and/or heat to desorb previously adsorbed $H_2S$. These adsorbents exhibit rapid kinetics for adsorption and desorption of $H_2S$.

The carbon adsorbent in various embodiments is stable at temperature of 150° C. and higher, e.g., at temperature in a range of from 150° C. to 180° C. The adsorbent in various embodiments exhibits a physical robustness, e.g., a single pellet radial crush strength of greater than 9 kilopond (kP) as measured by the procedure of American Society of Testing Materials (ASTM) method D4179.

The adsorbent of the disclosure may include porosity of any suitable pore size and pore size distribution characteristics that impart requisite hydrogen sulfide adsorptive capacity to the adsorbent. In various embodiments, the carbon adsorbent comprises porosity including pores the majority of which are less than 2 nm in diameter. For example, the carbon adsorbent can include porosity in which at least 40% of the pores of the porosity have pore size in a range of from 0.2 nm to 1.5 nm.

The carbon adsorbent of the present disclosure is advantageously formed as a pyrolysis product of a pyrolyzable starting material. The pyrolyzable starting material can be of any suitable type that by undergoing pyrolysis for sufficient time and at sufficient temperature conditions yields a pyrolysis product with porosity that is effective for adsorption of hydrogen sulfide. The starting material can be any of various pyrolyzable resins, e.g., resins such as polyethylene or other polyolefins, phenolic resins, acrylic resins, polyurethane resins, chloro- or fluoropolymer resins such as polyvinyl chloride, polyvinylidene chloride, polyvinylidene fluoride, polytetrafluoroethylene, etc., as well as copolymers of monomers of the foregoing polymers. In various embodiments, the starting material comprises polyvinylidene chloride (PVDC) or polyvinylidene fluoride (PVDF). In other embodiments, the starting material comprises copolymer blends of PVDC or PVDF with other polymers for improved processing and handling benefits that are well known in the industry.

The pyrolyzable starting material is subjected to pyrolysis to carbonize the starting material and form the carbon pyrolyzate adsorbent, at suitable process conditions and for sufficient time to achieve the desired properties herein disclosed, including selectivity for carbon dioxide over methane when both are present in the gas mixture contacted with the adsorbent. The process conditions, including temperature, pressure, duration, etc. are readily determined within the skill in the art based on the disclosure herein, to achieve the specific carbon pyrolyzate adsorbent of the present disclosure. Such determination may involve preparation of pyrolyzates of the starting material as processed at successively varying conditions to establish a set of process conditions that yields the desired adsorbent material.

Another aspect of the disclosure relates to an apparatus for removing hydrogen sulfide from a hydrogen sulfide-containing gas, in which the apparatus comprises a vessel containing the carbon adsorbent of the present disclosure, wherein the vessel is adapted for contacting of the gas with the carbon adsorbent to effect adsorption of hydrogen sulfide by the adsorbent, to yield a hydrogen sulfide-reduced gas. The vessel may be arranged for flow of the hydrogen sulfide-containing gas therethrough. The vessel may for example comprise a canister through which the hydrogen sulfide-containing gas can be flowed.

In a further aspect, the disclosure relates to an apparatus for removing hydrogen sulfide from a gas mixture including same, in which such apparatus comprises at least one adsorbent bed of carbon pyrolyzate adsorbent of the disclosure that is selective for hydrogen sulfide in contact with the gas mixture, and the at least one adsorbent bed is arranged (i) for contacting with the gas mixture during a first period of time to adsorb hydrogen sulfide on the carbon adsorbent in the bed, and discharge from the bed a hydrogen sulfide-reduced methane gas, and (ii) for desorbing previously adsorbed hydrogen sulfide from the carbon adsorbent in the bed during a second period of time.

In such apparatus, each of the at least one adsorbent bed(s) may be disposed in an adsorber vessel through which the gas mixture is arranged flow during the first period of time, and which is arranged for desorption of hydrogen sulfide from the carbon adsorbent in the bed during the second period of time. The vessels may be manifold together with inlet and outlet manifolds each of which is valved and arranged for corresponding operation in which one of the vessels is on-stream while the other is off-stream, being regenerated or in standby condition awaiting renewal of the on-stream operation, so that each of the multiple vessels progresses through a cycle in an alternating, repeating manner.

For example, the adsorption system apparatus may comprise at least two adsorber vessels, arranged for cyclic alternating and repetitive operation in which at least one of the adsorber vessels is/are adsorbing hydrogen sulfide from the gas mixture on the carbon adsorbent bed therein, while at least one other of said adsorber vessels is/are desorbing previously adsorbed hydrogen sulfide from the carbon adsorbent bed therein, or is in standby operation awaiting resumption of adsorbing operation.

The multiple vessels may be configured and arranged for any suitable cyclic operation. For example, they may be configured and arranged for pressure or vacuum swing operation, temperature swing operation, or combined temperature/pressure swing operation. The carbon adsorbent in the respective beds in the adsorption system apparatus can be of any suitable character as described above for the adsorbent of the present disclosure.

In one embodiment, wherein the adsorbent vessels are adapted for cyclic repeating operation in which each of at least two adsorbent vessels is conducted through a cycle of on-stream operation and off-stream operation in the cyclic repeating operation, and each of the adsorbent vessels is constructed and arranged for regeneration in the off-stream operation, the regeneration operation can include at least one of the operations of:

vacuum desorption of the carbon adsorbent;
pressure swing desorption of the carbon adsorbent;
direct or indirect heating of the carbon adsorbent;
thermal swing desorption of the carbon adsorbent; and
contacting of the carbon adsorbent with a non-sorbable gas, producing a concentration gradient effecting desorption of previously adsorbed hydrogen sulfide from the carbon adsorbent.

The apparatus for hydrogen sulfide adsorption in a specific embodiment applicable to petroleum refining operations generating flowable hydrocarbonaceous material and associated hydrogen sulfide-containing gas, comprises: a material collection tank for receiving the flowable hydrocarbonaceous material having hydrogen sulfide-containing gas associated therewith; first flow circuitry for interconnecting a source of the flowable hydrocarbonaceous material having hydrogen sulfide-containing gas associated therewith with the material collection tank; second flow circuitry arranged to flow hydrogen sulfide-containing gas from the material collection tank to the vessel containing the carbon adsorbent; and a motive fluid driver arranged to effect flow through the first flow circuitry of the flowable hydrocarbonaceous material having hydrogen sulfide-containing gas associated therewith from the source to the material collection tank, and to effect flow of the hydrogen sulfide-containing gas through the second flow circuitry from the material collection tank to the vessel containing the carbon adsorbent to adsorb hydrogen sulfide from the hydrogen sulfide-containing gas on the carbon adsorbent to produce hydrogen sulfide-reduced gas for discharge from the vessel.

The motive fluid driver in the apparatus may be of any suitable type, and can for example comprise a device selected from among pumps, compressors, fans, blowers, ejectors, eductors, and venturis. In various embodiments, the motive fluid driver can be a vacuum pump.

In the above-described apparatus, the material collection tank may be mounted on a motive vehicle, e.g., a truck. The apparatus may be constructed and arranged, with the first flow circuitry, second flow circuitry, and vessel being carried on the motive vehicle. The vessel may be arranged in such apparatus to discharge the hydrogen sulfide-reduced gas to an ambient environment of the vessel, e.g., the atmosphere, in instances in which substantially complete removal of hydrogen sulfide has been effected, to produce a substantially hydrogen sulfide-free effluent.

A further aspect the disclosure relates to a method of making a carbon adsorbent of the present disclosure, such method comprising pyrolyzing a pyrolyzable starting material for sufficient time under sufficient pyrolysis conditions to yield the carbon adsorbent. The pyrolyzable starting material can be of any suitable type, and for example can comprise a resin selected from the group consisting of polyethylene, polyolefins, phenolic resins, acrylic resins, polyurethane resins, chloropolymer resins, fluoropolymer resins, polyvinyl chloride, polyvinylidene chloride, polyvinylidene fluoride, polytetrafluoroethylene, and copolymers of monomers of the foregoing resins.

In one embodiment, the starting material comprises PVDF, in another PVDC, and in yet another a copolymer blend of PVDF or PVDC with another polymer which is added to aid in processing and handling.

Another aspect of the disclosure relates to a method of removing hydrogen sulfide from a gas mixture including same, in which such method comprises contacting the gas mixture with a carbon pyrolyzate adsorbent of the present disclosure, to adsorb hydrogen sulfide from the gas mixture on the adsorbent and yield a hydrogen sulfide-reduced gas.

In such method, the gas mixture may for example comprise gas associated with flowable hydrocarbonaceous material, e.g., deriving from a petroleum refining process. In another application, the gas mixture may comprise effluent gas from a biomass digester. In yet another embodiment the gas mixture could be a syngas product generated by the gasification of coal in an Integrated Gasification Combined Cycle (IGCC) process in a power generation plant. The gas mixture in still another implementation may comprise a natural gas mixture containing hydrogen sulfide.

In the above-described method, the carbon pyrolyzate adsorbent subsequent to adsorption of hydrogen sulfide thereon, can be regenerated by appropriate regeneration process to renew the adsorbent for resumed contacting of the gas mixture therewith. Such regeneration process can comprise one or more of the operations selected from the group consisting of:
vacuum desorption of the carbon adsorbent;
pressure swing desorption of the carbon adsorbent;
direct or indirect heating of the carbon adsorbent;
thermal swing desorption of the carbon adsorbent; and
contacting of the carbon adsorbent with a non-sorbable gas, producing a concentration gradient effecting desorption of previously adsorbed hydrogen sulfide from the carbon adsorbent.

The method of removing hydrogen sulfide from gas mixtures containing same can be carried out in an implementation in which the carbon adsorbent is contained in a vessel arranged for flow of the gas mixture therethrough to effect the contacting. The vessel can for example comprise a canister through which the gas mixture is flowable.

The foregoing method can be carried out in an arrangement in which the carbon adsorbent is contained in at least two adsorbent vessels each containing an adsorbent bed of the carbon adsorbent, wherein the at least two adsorbent vessels are manifolded together with inlet and outlet manifolds each of which is valved and arranged for operation in which at least one of the adsorber vessels is/are on-stream, while at least one other is/are off-stream and undergoing regeneration or in standby condition, awaiting renewal of on-stream operation, with the adsorbent vessels being adapted for cyclic repeating operation wherein each of the at least two adsorbent vessels is conducted through a cycle of on-stream operation and off-stream operation in the cyclic repeating operation. The cyclic repeating operation can for example include pressure or vacuum swing operation, temperature swing operation, or combined temperature/pressure swing operation.

The disclosure in another aspect relates to a process for capture of hydrogen sulfide present in a gas associated with a flowable hydrocarbonaceous material, such process comprising: separating the hydrogen sulfide-containing gas from the hydrocarbonaceous material; and contacting the hydrogen sulfide-containing gas with a carbon adsorbent of the present disclosure so that the carbon adsorbent adsorbs the hydrogen sulfide from the hydrogen sulfide-containing gas to yield hydrogen sulfide-reduced gas.

Such hydrogen sulfide capture process can further comprise regenerating the carbon pyrolyzate adsorbent subsequent to adsorption of hydrogen sulfide thereon, to renew the adsorbent for resumed contacting, wherein the regenerating comprises at least one regeneration method selected from the group consisting of:

(1) vacuum or reduced pressure desorption of hydrogen sulfide from the carbon adsorbent;
(2) heating the carbon adsorbent with a heat transfer medium that is flowed through a heating jacket in thermal contact with the adsorbent to desorb hydrogen sulfide therefrom;
(3) direct heating of the adsorbent by contacting the carbon adsorbent with heated gas or vapor, to desorb hydrogen sulfide therefrom;
(4) electrically resistively heating the carbon adsorbent in a direct or indirect manner, to desorb hydrogen sulfide therefrom; and
(5) flowing a non-sorbable gas in contact with the carbon adsorbent to generate a concentration gradient effecting desorption of hydrogen sulfide from the adsorbent.

The regenerating can for example comprise heating of the adsorbent by contacting the carbon adsorbent with heated gas, to desorb hydrogen sulfide therefrom, such as where the heating gas comprises waste heat exhaust from a vehicle.

Such arrangement for regeneration of the adsorbent using vehicle waste heat exhaust is usefully employed for cleaning or vacuuming of "slop oil" storage tanks, which as discussed in the Background section hereof can contain a myriad of different hydrocarbons, water, and $H_2S$. Such storage tanks are typically serviced by vacuum pumper trucks that vacuum pump the hydrocarbonaceous material and associated hydrogen sulfide-containing gas from the petroleum refineries storage tanks, and that heretofore have discharged the extracted hydrogen sulfide-containing gas to the atmosphere. The present disclosure contemplates the further treatment of such extracted hydrogen sulfide-containing gas by sorptive processing of the gas using the carbon adsorbent of the present disclosure, to remove the hydrogen sulfide from the gas before it is vented to the environment.

In accordance with the present disclosure, the vacuum pumper truck may have integrated therewith a bed of the carbon adsorbent of the present disclosure, e.g., in a vessel containing same through which the hydrogen sulfide-containing gas is flowed for contacting with the carbon adsorbent, or in which a canister containing such adsorbent is disposed in a vessel of such type, so that the carbon pyrolyzate adsorbent, once it has become loaded to a predetermined extent with hydrogen sulfide, can simply be changed out, and a fresh canister installed to accommodate further processing of the hydrogen sulfide-containing gas extracted in the vacuum pumping operation. The canister can for example be a porous container through which the hydrogen sulfide-containing gas can be flowed to contact the adsorbent. In one embodiment, the canister is a wire mesh basket accommodating such gas flow. In another embodiment, the canister comprises a cylindrical can with fluid inlet and outlet ports at its respective ends, to accommodate flow of hydrogen sulfide-containing gas therethrough.

While primarily described herein as applicable to the adsorption and capture of hydrogen sulfide, carbon adsorbents of the disclosure can be employed for other adsorption applications, such as gas separations, capture, or abatement applications in a variety of different industrial processes, including, but not limited to, $CO_2$ capture, $CO_2$ separation from $CH_4$, $C_2H_6$ separation from $CH_4$, $PH_3$ capture, biogas upgrading, and syngas purification.

Figure 1:
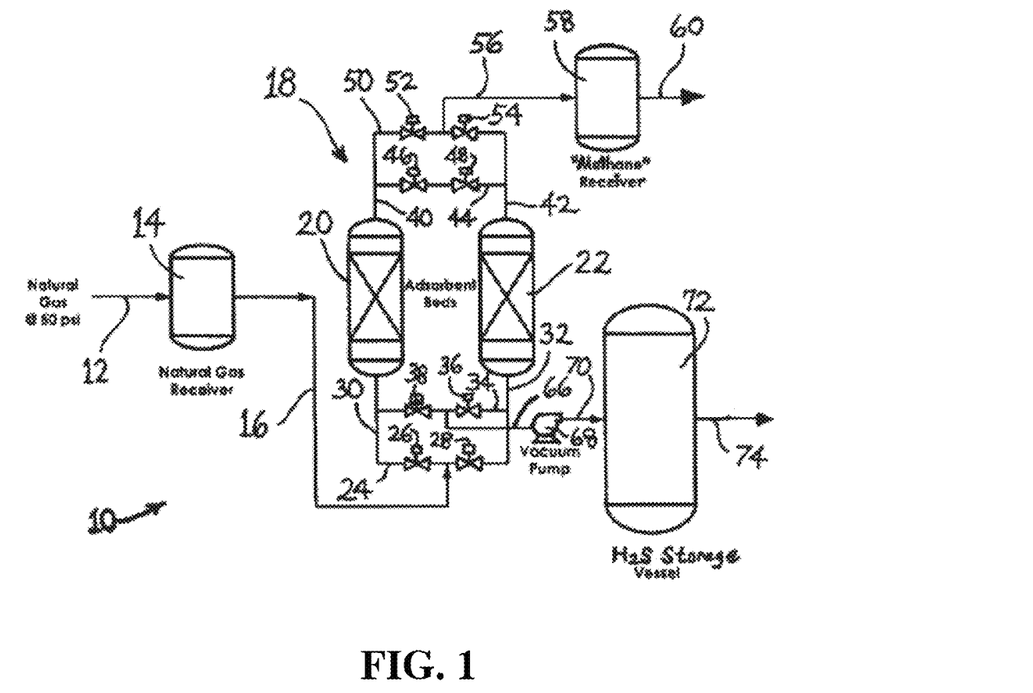
FIG. 1 is a schematic representation of a process system for removing hydrogen sulfide from natural gas containing carbon dioxide, according to one embodiment of the present disclosure.

Referring now to the drawings, FIG. 1 is a schematic representation of a process system 10 for adsorptive removal of hydrogen sulfide from natural gas containing same, utilizing the carbon adsorbent of the present disclosure.

As illustrated, natural gas containing hydrogen sulfide, e.g., at 50 psi pressure, is introduced to the system in a feed line 12 and flows to the surge vessel 14 ("Natural Gas Receiver"), which provides a buffering vessel to accommodate variations in volumetric flow rate of the influent natural gas. From the surge vessel 14, the influent natural gas flows in line 16 to the feed manifold 24 of the hydrogen sulfide removal system 18. The hydrogen sulfide removal system 18 comprises adsorbent beds in adsorber vessels 20 and 22. The adsorber vessels are manifolded to one another, at their inlet ends, by feed manifold 24 containing flow control valves 26 and 28, feed/discharge lines 30 and 32, and hydrogen sulfide extraction manifold 34 containing flow control valves 36 and 38, and at their outlet ends, by a discharge manifold 50 containing flow control valves 52 and 54, flow equalization manifold 44 containing flow control valves 46 and 48, and feed/discharge lines 40 and 42.

Joined to the hydrogen sulfide extraction manifold 34 is a hydrogen sulfide discharge line 66 coupled to vacuum pump (or other motive fluid driver) 68, which in turn discharges the hydrogen sulfide in discharge line 70 to the hydrogen sulfide storage vessel 72. The hydrogen sulfide storage vessel 72 has a hydrogen sulfide effluent line 74.

The process system 10 also includes a methane discharge line 56 joined to discharge manifold 50 for flowing the hydrogen sulfide-reduced natural gas (methane gas) to the "Methane" Receiver 58, which serves as a surge tank for the hydrogen sulfide-reduced natural gas received from the hydrogen sulfide removal system 18. The "Methane" Receiver tank 58 is arranged to discharge hydrogen sulfide-reduced natural gas in line 60.

The product hydrogen sulfide-reduced natural gas may be flowed to a downstream use or other disposition facility, such as a chemical synthesis facility, natural gas pipeline or transport facility, or other natural gas-utilizing process facility, or may be recycled for further upgrading.

In the hydrogen sulfide removal system 18, the on-stream one of the adsorber vessels 20 and 22 receives the influent natural gas, and produces hydrogen sulfide-reduced natural gas that flows to the surge vessel 58, from which it is discharged from the system.

It will be recognized that the various valves in the inlet and outlet manifolds of the hydrogen sulfide removal system 18 will be modulated as to their open/closed positions, to effectuate the continuous operation and cyclic alternating adsorption and desorption steps in the respective adsorber vessels. This modulation can be done at a pre-determined frequency, or optionally an in-stream sensor can be employed to determine hydrogen sulfide breakthrough of the on-stream adsorbent bed(s) and trigger the cyclic alternating to the unsaturated or regenerated bed(s). This smart sensing and feedback system may have tactical or performance advantages in processes where the hydrogen sulfide concentration level is not known in advance or is variable.

Figure 2:
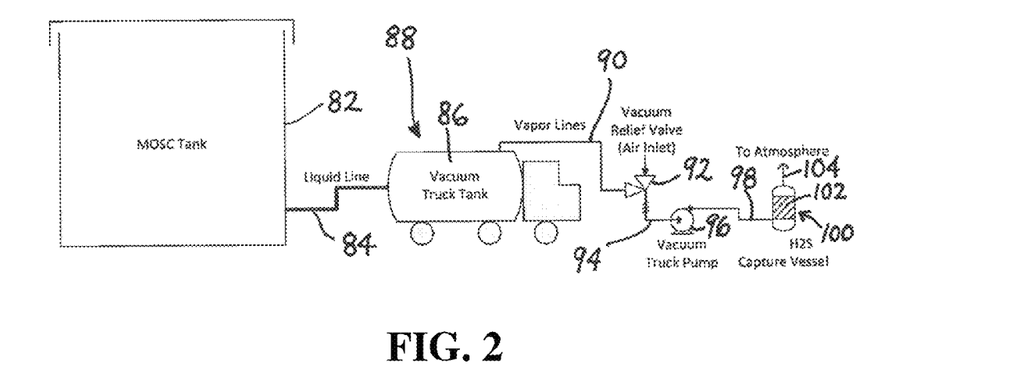
FIG. 2 is a schematic representation of a process system for capturing hydrogen sulfide from a vacuum pump effluent in the disposition of miscellaneous oily sludge coking (MOSC) waste from a petroleum refining operation.

FIG. 2 is a schematic representation of a process system for capturing hydrogen sulfide from a vacuum pump effluent in the disposition of miscellaneous oily sludge coking (MOSC) waste from a petroleum refining operation.

The MOSC tank 82 of the petroleum refining operation is illustrated as being emptied by a vacuum tank truck 88 including a vacuum tank 86 that is coupled by a liquid line 84 to the MOSC tank. The truck 88 includes a vapor line 90 interconnecting the vacuum tank 86 with a vacuum relief valve 92 and, via feed line 94, vacuum truck pump 96. Although shown separately for ease of illustration, it will be recognized that the vapor line 90, vacuum relief valve 92, feed line 94, and vacuum truck pump 96 can in practice be integrated on the truck 88.

The vacuum truck pump 96 is connected to a discharge line 98 for flowing extracted gas to a hydrogen sulfide capture vessel 100. The hydrogen sulfide capture vessel 100 contains a bed 102 of carbon pyrolyzate adsorbent in accordance with the present disclosure. The hydrogen sulfide-containing gas thus is extracted from the headspace in the vacuum tank 86 of truck 88 and flowed under the action of pump 96 through vapor line 90, feed line 94, and discharge line 98 to the hydrogen sulfide capture vessel 100.

The hydrogen sulfide-containing gas introduced to the hydrogen sulfide capture vessel 100 flows upwardly through carbon adsorbent bed 102, which functions to adsorb hydrogen sulfide from the gas, to yield a hydrogen sulfide-depleted gas that is discharged from the vessel 100 in discharge line 104 to the atmosphere.

The hydrogen sulfide capture vessel 100, although shown as being separate from the vacuum truck 88, in the schematic drawing of FIG. 2, may be likewise integrated on the truck, and may for example comprise an arrangement in which the bed 102 is constituted in a flow-through removable canister that may be introduced to the vessel 102, and changed out when the carbon adsorbent in the bed becomes finally loaded with hydrogen sulfide.

Alternatively, the carbon adsorbent in the vessel 102 may be present in a fixed bed 102 that is contacted with hydrogen sulfide-containing gas flowed therethrough until it is finally loaded with hydrogen sulfide to a predetermined extent, following which the adsorbent may be regenerated to renew it for reuse, involving contacting of hydrogen sulfide-containing gas therewith.

In the FIG. 2 system, the vacuum pump 96 is used to draw vacuum on the truck tank 86 to create a pressure differential between the truck tank and the MOSC tank 82. This pressure differential then causes liquid flow into the truck tank from the MOSC tank. The vacuum relief valve 92 is employed to prevent excessive vacuum level and potential implosion of the truck tank by bleeding air into the pumping system so as to maintain a set vacuum level, e.g., a vacuum pressure of approximately 50 kPa.

The carbon adsorbent in the bed 102 is effective to capture the hydrogen sulfide in the gas drawn from the vapor headspace of the vacuum truck tank 86, as well as volatile organic compounds (VOCs) therein. In one specific embodiment, the hydrogen sulfide capture vessel 100 is constructed of 10 inch (0.254 m) diameter pipe having a height of 5 feet (1.524 m), and is provided with a flanged top end cap to allow for charging of the adsorbent. Such vessel may have three-inch (7.62 cm) inlet and outlet ports at its lower and upper ends, respectively. The inlet port may extend into the main body of the capture vessel and be provided with a perforate structure to distribute the hydrogen sulfide-containing gas over the full cross-sectional area of the bed for upward flow therethrough.

As mentioned, once the adsorbent becomes loaded with hydrogen sulfide, the adsorbent needs to be regenerated for further use. Any of various suitable regeneration methods may be utilized, in which previously adsorbed hydrogen sulfide is desorbed from the bed, discharged from the capture vessel and thereafter subjected to further treatment, disposition, or use. For example, the hydrogen sulfide-loaded carbon adsorbent can be regenerated by one or more of the following desorption regeneration techniques:

(1) vacuum or reduced pressure desorption of the carbon adsorbent, by imposition of vacuum pressure, e.g., a pressure below $1.0\times10^{-3}$ torr (0.133 Pa);
(2) disposing a jacket around the hydrogen sulfide capture vessel through which a heat transfer medium, e.g., steam, can be flowed to heat the adsorbent bed and cause desorption of hydrogen sulfide therefrom;
(3) direct heating of the adsorbent bed by passage of steam directly therethrough, to effect desorption of the adsorbed gas;
(4) embedding metal coils in the adsorbent bed and passing heat transfer medium such as steam through such coils, to cause liberation of adsorbed gas from the bed;
(5) deploying resistive heating elements within the capture vessel, to heat the adsorbent bed, and thereby cause liberation of the adsorbed gas from the adsorbent;
(6) passage of electrical current through the adsorbent bed, utilizing the carbon pyrolyzate adsorbent itself as a resistive medium, causing the bed to undergo heating, and in turn causing liberation of the adsorbed gas from the adsorbent;
(7) disposing a jacket around the vessel or metal coils throughout, in which waste heat exhaust from the vacuum truck engine or other available source can flow, to heat the adsorbent bed for desorption of previously adsorbed gas therefrom; and
(8) flowing an inert or otherwise non-sorbable gas, e.g., nitrogen, argon, helium, etc., through the bed to create a concentration gradient effecting desorption of the previously adsorbed gas from the adsorbent.

It will be recognized that the hydrogen sulfide capture system shown in FIG. 2 can be widely varied in practice, to effect removal of hydrogen sulfide from a gas mixture containing same, so that the resulting hydrogen sulfide-reduced gas can be discharged to the atmosphere with negligible sulfur content.

It will be further recognized that the above-described regeneration modes discussed in connection with the FIG. 2 embodiment may also be utilized in the FIG. 1 embodiments, as well as in the general practice of the present disclosure.

Figure 3:
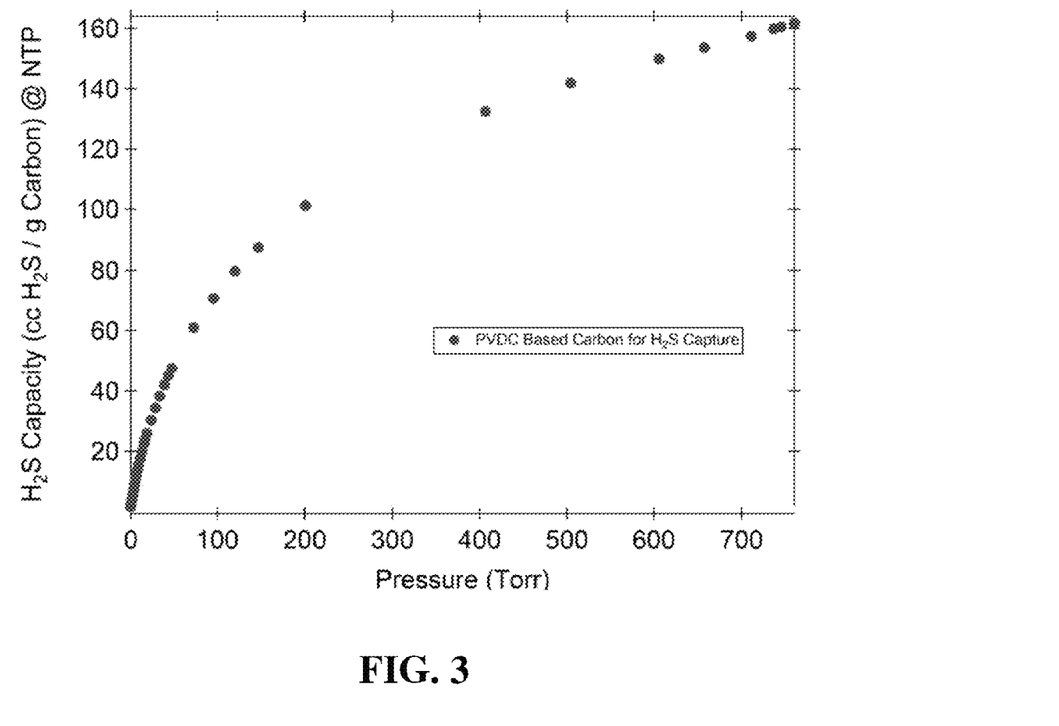
FIG. 3 is an adsorption isotherm plot of capacity of a PVDC carbon adsorbent for hydrogen sulfide, in cc $H_2S$/gram adsorbent, as a function of pressure, in torr.

FIG. 3 is an adsorption isotherm plot of a PVDC carbon adsorbent of the present disclosure, showing its capacity for hydrogen sulfide, in cc $H_2S$/gram adsorbent, as a function of pressure, in Torr. Such PVDC carbon pyrolyzate adsorbent was in a particulate form, of carbon tablets having a diameter of 3.2 mm and thickness of 2.18 mm, with a bulk density between 0.65 and 0.73 g per cc. Its capacity for hydrogen sulfide is greater than 150 cc per gram at normal conditions (293.15° Kelvin and 760 Torr (101.325 kPa)).

Figure 4:
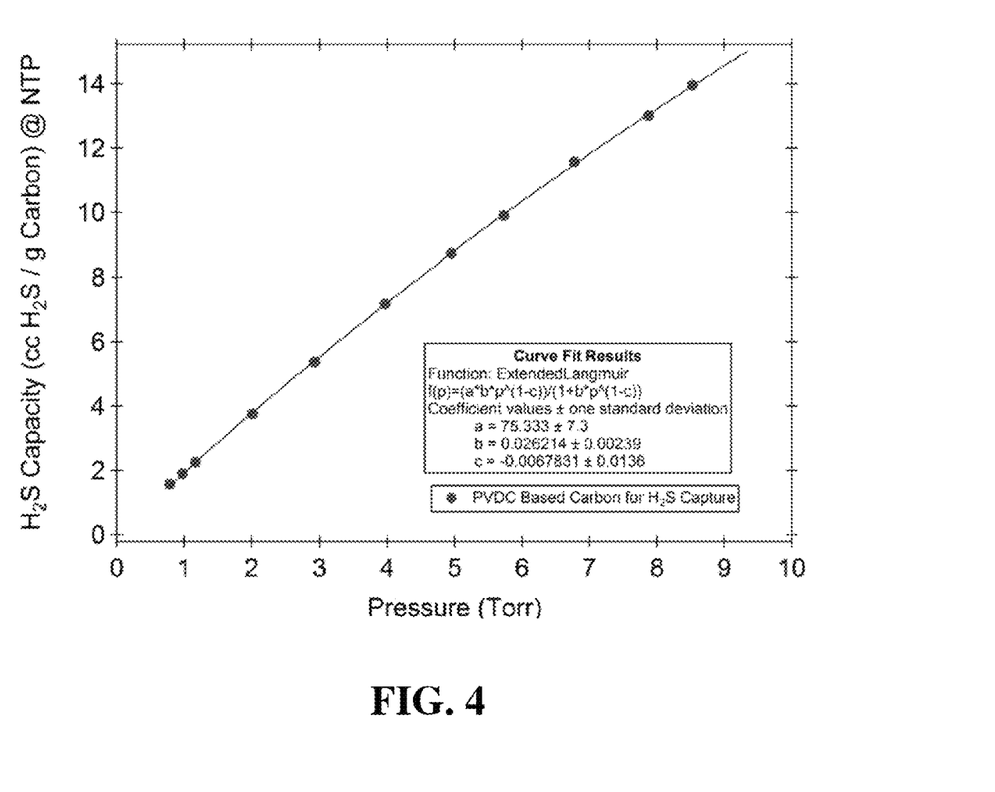
FIG. 4 is an adsorption isotherm plot of capacity of a PVDC carbon adsorbent for hydrogen sulfide, in cc $H_2S$/gram adsorbent, as a function of pressure, in torr, for low pressure conditions (0-10 torr).

FIG. 4 is an adsorption isotherm plot of capacity of the same PVDC adsorbent for hydrogen sulfide, in cc $H_2S$/gram adsorbent, as a function of pressure, in Torr, at low pressure conditions of 0-10 Torr (0-1.33 kPa). As shown, the hydrogen sulfide capacity is greater than 1.4 cc/gram at a partial pressure of 0.76 Torr (0.1 kPa), 1000 ppm of hydrogen sulfide at 293.15° Kelvin.

Such adsorbent of the isotherms of FIGS. 3 and 4 is stable up to temperatures of 180° C., and in pellet or tablet form has a radial crush strength of greater than 9 kilopond as measured by ASTM D4179 or in powdered form has an attrition rate index of less than 0.01 weight percent per hour as measured by ASTM D5757.

While the disclosure has been set out herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the invention as hereinafter claimed is intended to be broadly construed and interpreted, as including all such variations, modifications and alternative embodiments, within its spirit and scope.

What is claimed is:

1. A particulate carbon adsorbent having reversible sorptive affinity for capture of hydrogen sulfide from gas containing same, and the following characteristics:
    (a) a bulk density as measured by ASTM D2854 in a range of from 0.55 g/cc adsorbent to 0.65 g/cc adsorbent;
    (b) an $H_2S$ capacity in a range of from 140 cc $H_2S$/g adsorbent to 250 cc $H_2S$/g adsorbent, at normal conditions (1 atm, 293.15° K);
    (c) an $H_2S$ capacity in a range of from 1.0 cc $H_2S$/g adsorbent to 15.0 cc $H_2S$/g adsorbent, at partial pressure of 0.76 torr (101.3 Pa) (1000 ppm) of $H_2S$ at 293.15° K; and
    (d) a single pellet radial crush strength in a range of from 7 kilopond (kP) to 40 kilopond (kP) as measured by ASTM D4179.

2. The carbon adsorbent of claim 1, wherein:
    the bulk density is in a range of from 0.6 to 0.65 g/cc adsorbent;
    the $H_2S$ capacity at normal conditions (1 atm, 293.15° K) is in a range of from 150 cc/g adsorbent to 200 cc/g adsorbent; and
    the $H_2S$ capacity, at a partial pressure of 0.76 torr (101.3 Pa) (1000 ppm) of $H_2S$ at 293.15° K, is in a range of from 1.5 cc $H_2S$/g adsorbent to 10.0 cc $H_2S$/g adsorbent.

3. The carbon adsorbent of claim 1, comprising particles of particle size in a range of from 0.8 to 3.0 mm.

4. The carbon adsorbent of claim 1, having an average particle diameter in a range of from 1.0 to 5 mm.

5. The carbon adsorbent of claim 1, comprising porosity wherein a majority of pores are less than 2 nm in diameter, and wherein at least 40% of pores have pore size in a range of from 0.2 nm to 1.5 nm.

6. The carbon adsorbent of claim 1, comprising a pyrolyzate of a resin selected from the group consisting of polyethylene, polyolefins, phenolic resins, acrylic resins, polyurethane resins, chloropolymer resins, fluoropolymer resins, polyvinyl chloride, polyvinylidene chloride, polyvinylidene fluoride, polytetrafluoroethylene, and copolymers of monomers of the foregoing resins.

7. An apparatus for removing hydrogen sulfide from a hydrogen sulfide-containing gas, said apparatus comprising a vessel containing the carbon adsorbent of claim 1, wherein the vessel is adapted for contacting of said gas with the carbon adsorbent to effect adsorption of hydrogen sulfide by the adsorbent, to yield a hydrogen sulfide-reduced gas.

8. The apparatus of claim 7, comprising at least one adsorbent vessel containing an adsorbent bed of said carbon adsorbent, said at least one adsorbent vessel being arranged (i) for contacting with the hydrogen sulfide-containing gas during a first period of time to adsorb hydrogen sulfide on the carbon adsorbent in the bed, and discharge from the bed a hydrogen sulfide-reduced gas, and (ii) for desorbing previously adsorbed hydrogen sulfide from the carbon adsorbent in the bed during a second period of time.

9. The apparatus of claim 7, comprising at least two adsorbent vessels each containing an adsorbent bed of said carbon adsorbent, wherein the at least two adsorbent vessels are manifolded together with inlet and outlet manifolds each of which is valved and arranged for operation in which at least one of said adsorber vessels is/are on-stream, while at least one other is/are off-stream and undergoing regeneration or in standby condition, awaiting renewal of on-stream operation, and with the adsorbent vessels being adapted for cyclic repeating operation wherein each of the at least two adsorbent vessels is conducted through a cycle of on-stream operation and off-stream operation in said cyclic repeating operation, wherein each of the adsorbent vessels is constructed and arranged for regeneration in the off-stream operation, comprising a regeneration operation including at least one of the operations selected from the group consisting of:
   (i) vacuum desorption of the carbon adsorbent;
   (ii) pressure swing desorption of the carbon adsorbent;
   (iii) direct or indirect heating of the carbon adsorbent;
   (iv) thermal swing desorption of the carbon adsorbent; and
   (v) contacting of the carbon adsorbent with a non-sorbable gas, producing a concentration gradient effecting desorption of previously adsorbed hydrogen sulfide from the carbon adsorbent.

10. A method of making a carbon adsorbent as claimed in claim 1, comprising pyrolyzing a pyrolyzable starting material for sufficient time under sufficient pyrolysis conditions to yield said carbon pyrolyzate adsorbent, wherein said pyrolyzable starting material comprises a resin selected from the group consisting of polyethylene, polyolefins, phenolic resins, acrylic resins, polyurethane resins, chloropolymer resins, fluoropolymer resins, polyvinyl chloride, polyvinylidene chloride, polyvinylidene fluoride, polytetrafluoroethylene, and copolymers of monomers of the foregoing resins.

11. The method of claim 10, wherein said starting material comprises a PVDF polymer or copolymer, or a PVDC polymer or copolymer.

12. A method of removing hydrogen sulfide from a gas mixture including same, said method comprising contacting said gas mixture with a carbon adsorbent according to claim 1, to adsorb hydrogen sulfide from said gas mixture on said adsorbent and yield a hydrogen sulfide-reduced gas.

13. The method of claim 12, wherein said gas mixture including hydrogen sulfide comprises gas selected from the group consisting of:
   (a) gas deriving from a petroleum refining process;
   (b) gas deriving from a fluid catalytic cracking (FCC) unit;
   (c) gas deriving from gasification of sulfur-containing coal; and
   (d) gas deriving from a biomass digester.

14. The method of claim 12, wherein said carbon adsorbent subsequent to adsorption of hydrogen sulfide thereon, is regenerated by a regeneration process to renew said adsorbent for resumed contacting of said gas mixture therewith.

15. The method of claim 14, wherein said regeneration process comprises at least one of the operations selected from the group consisting of:
   (i) vacuum desorption of the carbon adsorbent;
   (ii) pressure swing desorption of the carbon adsorbent;
   (iii) direct or indirect heating of the carbon adsorbent;
   (iv) thermal swing desorption of the carbon adsorbent; and
   (v) contacting of the carbon adsorbent with a non-sorbable gas, producing a concentration gradient effecting desorption of previously adsorbed hydrogen sulfide from the carbon adsorbent.

16. The method of claim 12, as carried out in a process selected from the group consisting of pressure swing processes, vacuum swing processes, temperature swing processes, and combinations thereof.

17. A process for capture of hydrogen sulfide present in a gas associated with a flowable hydrocarbonaceous material, said process comprising:
   separating the hydrogen sulfide-containing gas from the hydrocarbonaceous material; and
   contacting the hydrogen sulfide-containing gas with a carbon adsorbent as claimed in claim 1, so that the carbon adsorbent adsorbs the hydrogen sulfide from the hydrogen sulfide-containing gas to yield a hydrogen sulfide-reduced gas.

18. The process of claim 17, further comprising regenerating the carbon adsorbent subsequent to adsorption of hydrogen sulfide thereon, to renew said adsorbent for resumed contacting.

19. The process of claim 18, wherein said regenerating comprises heating of the carbon adsorbent to effect desorption of hydrogen sulfide therefrom.

20. The carbon adsorbent of claim 1, comprising particles with diameter in a range of from 1 to 5 mm, with porosity wherein a majority of pores are less than 2 nm in diameter.

* * * * *